United States Patent [19]

Murase et al.

[11] Patent Number: 4,457,872
[45] Date of Patent: Jul. 3, 1984

[54] 2-HYDROXYOXANILIC ACID DERIVATIVES

[75] Inventors: Kiyoshi Murase, Saitama; Toshiyasu Mase, Chiba; Hideki Arima, Tokyo; Kenichi Tomioka, Saitama; Yoso Numasaki, Saitama, all of Japan

[73] Assignee: Yamanouchi Pharmaceutical Co., Tokyo, Japan

[21] Appl. No.: 416,317

[22] Filed: Sep. 9, 1982

Related U.S. Application Data

[63] Continuation of Ser. No. 208,299, Nov. 19, 1980, abandoned.

[30] Foreign Application Priority Data

Nov. 28, 1979 [JP] Japan ................................. 54-153935
Oct. 7, 1980 [JP] Japan ................................. 55-139297
Oct. 7, 1980 [JP] Japan ................................. 55-139298
Oct. 29, 1980 [JP] Japan ................................. 55-151816

[51] Int. Cl.$^3$ ..................... C07C 121/75; C07C 79/46
[52] U.S. Cl. ................................. 260/465 D; 560/22; 560/29; 560/43; 560/20; 424/304; 424/309; 564/167; 544/391; 562/452; 260/456 A
[58] Field of Search .............................. 560/43, 22, 29; 260/465 D

[56] References Cited

U.S. PATENT DOCUMENTS 3,966,965 6/1976 Sellstedt et al. ..................... 560/43
4,069,343 1/1978 Sellstedt et al. ..................... 560/43
4,160,100 7/1979 Sellstedt et al. ..................... 560/43

OTHER PUBLICATIONS

Thomae, Chem. Abst., vol. 58, p. 6839.
Sellstedt et al., Journal of Medicinal Chemistry, 1975, vol. 18, No. 9, pp. 926-933, IV.

Primary Examiner—Glennon H. Hollrah
Assistant Examiner—Bruce D. Gray
Attorney, Agent, or Firm—Burgess, Ryan & Wayne

[57] ABSTRACT

A novel 2-hydroxyoxanilic acid derivative shown by the following formula

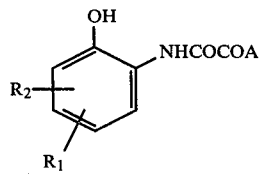

or a salt thereof. This compound possesses an immunoregulatory action and is useful as an antiallergic agent, an antiasthmatic, an antirheumatic, a carcinostatic agent, a therapeutic agent for autoimmune disease, and a suppressant of rejection at the tissue transplantation and skin graft.

4 Claims, No Drawings

2-HYDROXYOXANILIC ACID DERIVATIVES

This is a continuation, of application Ser. No. 208,299, filed Nov. 19, 1980 now abandoned.

DETAILED DESCRIPTION OF THE INVENTION

This invention relates to novel 2-hydroxyoxanilic acid derivatives. More particularly, the invention relates to the 2-hydroxyoxanilic acid derivatives shown by following formula I and the salts thereof

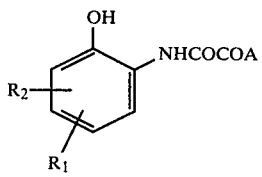

wherein A represents a hydroxyl group, a lower alkoxy group substitutable by a hydroxyl group, an amino group, a hydrazino group, a mono- or di-lower alkylamino group substitutable by an amino group, or a piperazino group substitutable by a lower alkyl group; $R_1$ represents a halogen atom, a nitro group, a lower alkyl group having 2 or more carbon atoms, an amino group, a mono- or di-lower alkylamino group, a hydroxyl group, a lower alkoxy group, a lower alkoxycarbonyl lower alkoxy group, a carboxy lower alkoxy group, a lower alkanoyloxy group, a lower alkanoyl group, an arylsulfonyloxy group, an

group (wherein $R_3$ represents a hydrogen atom, a lower alkyl group, a lower alkoxy group, a carboxy group, a lower alkoxycarbonyl group, or an amino group or a mono- or di-lower alkylamino group and $R_4$ represents a hydrogen atom or a lower alkyl group) or a group shown by

group (wherein X represents a oxygen atom and Y represents a hydroxyl group, a lower alkoxy group, or an amino group substitutable by lower alkyl group or phenyl lower alkyl group; said

also includes a cyano group); $R_1$ being, however, at the 5-position when $R_1$ is an

group and $R_1$ being at the 4-position or 5-position when $R_1$ is an

group; and $R_2$ represents a hydrogen atom, halogen atom, a nitro group, a lower alkyl group, an amino group, a mono- or di-lower alkylamino group, a hydroxyl group, a lower alkoxy group, a lower alkoxycarbonyl lower alkoxy group, a carboxy lower alkoxy group, a lower alkanoyloxy group, a lower alkanoyl group or an arylsulfonyloxy group.

In the general formula I described above, the term "lower" means a straight or branched carbon chain having 1-5 carbon atoms. Therefore, as the lower alkyl group for "a mono- or di-lower alkylamino group substitutable by an amino group", "a piperazino group substitutable by a lower alkyl group", "a mono- or di-lower alkylamino group, "a lower alkyl group", and "an amino group may have been substituted by phenyl lower alkyl group" shown by $R_1$, $R_2$ and A, included are a methyl group, ethyl group, propyl group, sec-butyl group, tert-butyl group, etc. Also, as the lower alkoxy group for "a lower alkoxy group substitutable by a hydroxyl group", "a lower alkoxy group", "a lower alkoxycarbonyl lower alkoxy group", "a carboxy lower alkoxy group", and "a lower alkoxycarbonyl group", included are a methoxy group, ethoxy group, propoxy group, isopropoxy group, butoxy group, etc. Furthermore, as the lower alkanoyl group for "a lower alkanoyloxy group" and "a lower alkanoyl group", included are a formyl group, acetyl group, propionyl group, butyryl group, isobutyryl group, etc.

As practical examples of "a lower alkyl group having 2 or more carbon atoms", included are a ethyl group, propyl group, isopropyl group, butyl group, sec-butyl group, isobutyl group, tert-butyl group, n-amyl group, tert-amyl group, etc. Also, as examples of "halogen atom", included are a fluorine atom, chlorine atom, bromine atom, iodine atom, etc., and as examples of "an arylsulfonyloxy group", included are a phenylsulfonyloxy group, tolylsulfonyloxy group, naphthylsulfonyloxy group, etc.

Then, the compounds of formula I provided by the invention may form the salts thereof. In other words, the desired compounds of this invention include their pharmaceutically acceptable salts. For example, there are the acid addition salts thereof with a mineral acid such as hydrochloric acid, hydrobromic acid, sulfuric acid, etc., or an organic acid such as methanesulfonic acid, p-toluenesulfonic acid, etc.; the salts thereof with an alkali metal such as sodium, potassium, etc., or an alkaline earth metal such as calcium, etc.; the ammonium salts thereof; and the salts thereof with an organic base such as methylamine, ethylamine, diethylamine, trimethylamine, triethylamine, pyridine, picoline, arginine, lysine, etc.

Although there are various kinds of compounds as oxanilic acid derivatives, they have been investigated mainly as medicaments for the antiallergic agents (e.g., U.S. Pat. Nos. 3,993,679; 4,017,538, 4,054,591; 4,069,343; 4,087,606; 4,089,973 and 4,095,028). As oxalinic acid derivatives possessing other pharmacological activities than an antiallergic activity, there are only some compounds which are useful in the prophylactic use in the treatment of gastric ulcer as disclosed in U.S. Pat. No. 4,137,325. In other words, none of the various oxanilic acid derivatives has been known to possess a strong immunoregulatory action.

Also, ethyl 2-hydroxyoxanilate, methyl 2-hydroxyoxanilate ("Chem. Abstr.", 57, p11207b), ethyl 2-hydroxy-5-methyloxanilate ("Chem. Abstr.", 58, p6840b), and 3-carboxy-2-hydroxy-5-nitrooxanilic acid esters (West German Pat. 2,746,385) are known as 2-hydroxyoxanilic acid derivatives. However, there are no disclosures in the aforesaid literatures about the uses of the former three compounds as medicament. On the last compounds described above, it is disclosed in the German patent that they possess an antiallergic action. However, the patent does not disclose that the aforesaid compounds affect the immune system and possess a strong immunoregulatory action.

The feature of the chemical structure in the compounds of this invention is in the point that the 2-position of oxanilic acid has been substituted by a hydroxyl group, and such 2-hydroxyoxanilic acid derivatives have a strong immunoregulatory action. Furthermore, those compounds are useful as an antiallergic agent, an antiasthamatic antirheumatic, a carcinostatic agent, a therapeutic agent for autoimmune disease, and suppressants of rejection at tissue transplantation and skin graft.

The compounds of this invention possess an immunoregulatory action.

The compounds of this invention which enhance the cellmediated immunity such as a delayed type hypersensitivity reaction and lymphocyte blastogenesis and-/or potentiate the humoral antibody formation are useful as a antirheumatics and a therapeutic agent of chronic hepatitis. Some of the compounds of this invention having immunostimulating action are effective for the protection and prophylaxis of virus or bacterial infections based on the reduction in immunity.

The compounds of this invention which inhibit the humoral antibody formation such as IgE antibody formation are useful as an antiallergic agent and an antiasthmatic since IgE antibody plays a key role in the Type I immediate hypersensitivity reaction.

Some of the compounds of this invention having an immunosuppressive action inhibit the passive cutaneous anaphylaxis (PCA) reaction in rat, suggesting they have an antiallergic action. In particular, the compounds of this invention showing a long lasting inhibitory effect in PCA test by oral administration in addition to the suppression of IgE antibody formation are useful as an antiallergic agent and an antiasthmatic.

The compounds of this invention which suppress the cellmediated immunity such as a delayed type hypersensitivity reaction are useful as an antiallergic agent, an antirheumatic, a therapeutic agent for autoimmune disease and a suppressant of rejection at the tissue transplantation and skin graft. In particular, the aforesaid compounds of this invention are useful in the treatment of delayed type hypersensitivity and rheumatoid arthritis.

Furthermore, some of the compounds of this invention inhibit the passive cutaneous anaphlaxis (PCA). Therefore, such compounds are useful as an antiallergic agent and an antiasthmatic.

Since the compounds of this invention have very low toxicity, they can be used as medicaments for various uses as described above.

The medical compositions which contain the compounds of this invention as the main component are formulated by a conventional manner using conventional carriers for formulation and excipients. The medicaments may be administered orally as tablets, pills, capsules, granules, etc., or may be administered parenterally as injections such as by intravenous injection, intramuscular injection, etc., or as aerosol, suppositories, etc. The doses of the medicaments are properly arranged according to each case on considering the symptom and age of the patients, sex distinction, etc., but are usually 5–600 mg per day for an adult in the case of oral administration and 1–300 mg per day for adult in the case of parenteral administration. The medicaments are administered 2–3 times a day.

The compounds of this invention shown by formula I are prepared by reacting an aminophenol shown by formula II

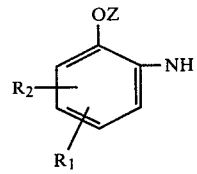

wherein Z represents a hydrogen atom or a protective group for a hydroxyl group and $R_1$ and $R_2$ have the same significance as in formula I and the oxalylic acid shown by formula III $$A-COCOOH \qquad III$$

wherein A has the same significance as in formula I or a reactive derivative thereof, by an ordinary manner, to form an oxalylate and, when Z is a protective group for the hydroxyl group, removing the protective group by a conventional procedure.

As the reactive derivative of an oxalylic acid, an oxalyl halide such as oxalyl chloride, etc., is usually used and in this case, the reaction is performed in a suitable solvent such as benzene, methylene chloride, tetrahydrofuran, etc., preferably in the presence of a base such as pyridine, dimethylaniline, potassium carbonate, sodium carbonate, etc. The reaction temperature is room temperature or lower, preferably lower than 10° C.

When the diaminophenol shown by formula II'

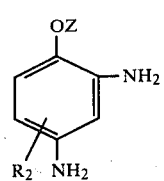

wherein $R_2$ and Z have the same significance as described above is used as the aminophenol of formula II in this process, these two amino groups are oxalylated. As the protective group for hydroxyl group of the aminophenol of formula II, a benzyl group is usually used and in this case the protective group (benzyl group) is removed by reduction, e.g., catalytic reduction in a conventional procedure.

As another process of producing the compounds of this invention shown by formula I, there is a process of mutually transforming the desired compounds. For the purpose, there are illustrated (1) hydrolysis of the ester, (2) ester interchange, (3) amination of the ester, (4) reduction of the nitro group, (5) acylation of the amino group, and (6) halogenation. These reactions are all performed by conventional procedures.

(1) By the hydrolysis of ester, a compound of formula I wherein A is, for example, an ethoxy group, is converted into a compound of formula I wherein A is a hydroxyl group. This reaction is usually performed under an alkaline condition.

(2) By the ester interchange, a compound of formula I wherein A is, for example, an ethoxy group, is converted into the group of formula I wherein A is a propoxy group, an isopropoxy group, a butoxy group or a 2-hydroxyethoxy group. This reaction is usually preformed by heating the former compound in a corresponding alcohol in the presence of an acid catalyst such as p-toluenesulfonic acid.

(3) By the amination of ester, a compound of formula I wherein A is, for example, an ethoxy group is converted into a compound of formula I wherein A is an amino group, a methylamino group, an ethylamino group, a 2-aminoethylamino group, a hydrazino group, or a 4-methylpiperazino group. This reaction is usually performed by reacting the former compound with a corresponding amine in a suitable solvent such as methanol, etc.

(4) By the reduction of the nitro group, a compound of formula I wherein at least one of $R_1$ and $R_2$ is a nitro group is converted into the compound of formula I wherein at least one of $R_1$ and $R_2$ is an amino group. This reaction is usually performed by catalytically reducing the former compound.

(5) By the acylation of the amino group, a compound of formula I wherein $R_1$ is an amino group or a mono-lower alkylamino group is converted into the compound of formula I wherein $R_1$ is an

group (wherein $R_3$ and $R_4$ have the same significance as described above). This acylation is performed by reacting a compound of formula I wherein $R_1$ is an amino group or a mono-lower alkylamino group with a carboxylic acid of the formula $R_3COOH$ or a reactive derivative thereof. As the reactive derivative of the carboxylic acid shown by $R_3COOH$, there are illustrated an acid anhydride, an acyl halide, etc. Suitable examples include acetic anhydride, ethyl chlorocarbonate, methyl isocyanate, etc. This reaction can be performed as in the case of aforesaid oxalylation by using the condition usually employed for acylation. When a free carboxylic acid ($R_3COOH$) is used, usually the reaction is carried out in the presence of a coupling agent, e.g. dicyclohexylcarbodiimide.

(6) By the halogenation, a compound of formula I wherein $R_2$ is hydrogen atom is converted into the compound of formula I wherein $R_2$ is a halogen atom. This reaction is performed by treating with a halogenating agent, such as bromine, chlorine, iodine, etc., by conventional procedures.

The compounds of this invention prepared as described above are isolated and purified by a conventional chemical operation usually employed in the field of the art, such as recrystallization, extraction, various kinds of chromatography, etc.

Then, the experimental results indicating the excellent pharmacological effects of the compounds of this invention are shown below.

Activity to delayed type hypersensitivity of mice:

Seven week old ICR-SLC mice (Shizuoka Agric. Coop. Assoc.) were sensitized by painting 0.1 ml of 7% picryl chloride (PC) solution in absolute ethanol on the shaved abdomen. After the 7 day sensitization period, the mice were challenged by painting 0.02 ml of 1% picryl chloride solution in olive oil on the inside of each ear. The ear thickness was measured with a dial thickness gauge. The increase in ear thickness was calculated as the difference between the value measured before challenge and at 24 hours thereafter. The test compounds were administered orally from day 0 to day 3 after the immunization. The results are shown in Table I.

TABLE I

| Drug | Dose (mg/kg P.O.) | N | Ear thickness increment (1/100 mm) | Increase (%) |
|---|---|---|---|---|
| ethyl 5-chloro-2-hydroxyoxanilate (Example 1) | 50 | 5 | 7.6 ± 0.6 | 46.2 |
|  | 400 | 5 | 7.5 ± 1.8 | 44.2 |
| Control | — | 10 | 5.2 ± 0.7 | — |
| ethyl 5-ethyl-2-hydroxyoxanilate (Example 3) | 50 | 5 | 9.7 ± 0.5 | 59.0 |
| Control | — | 10 | 6.1 ± 0.8 | — |
| ethyl 5-fluoro-2-hydroxyoxanilate (Example 14) | 400 | 5 | 4.7 ± 0.4 | 46.9 |
| Control | — | 10 | 3.2 ± 0.5 | — |
| n—propyl 5-chloro-2-hydroxyoxanilate (Example 18) | 50 | 5 | 4.5 ± 0.4 | 40.6 |
| Control | — | 10 | 3.2 ± 0.4 | — |
| 5-chloro-2-hydroxy-N—methyloxanilamide (Example 27) | 50 | 5 | 4.7 ± 0.5 | 46.9 |
| Control | — | 10 | 3.2 ± 0.5 | — |
| ethyl 5-amino-2-hydroxyoxanilate hydrochloride (Example 31) | 12.5 | 5 | 4.9 ± 0.4 | 53.1 |
|  | 100 | 5 | 4.5 ± 0.5 | 40.6 |
| Control | — | 10 | 3.2 ± 0.5 | — |
| ethyl 5-acetamido-2-hydroxyoxanilate (Example 33) | 50 | 5 | 4.9 ± 0.8 | 53.1 |
|  | 400 | 5 | 4.8 ± 0.8 | 50.0 |
| Control | — | 10 | 3.2 ± 0.5 | — |
| ethyl 5-formamido-2-hydroxyoxanilate (Example 34) | 50 | 5 | 5.7 ± 1.1 | 39.0 |
| Control | — | 10 | 4.1 ± 0.5 | — |
| 1-(5-cyano-2-hydroxyoxanilyl)-4-methylpiperazine (Example 44) | 400 | 5 | 5.1 ± 0.7 | 37.8 |
| Control | — | 10 | 3.7 ± 0.5 | — |

The above experimental results show that the compounds of this invention shown by formula I increase markedly the delayed type hypersensitivity reaction, which shows clearly that the compounds of this invention possess a strong immunostimulating action.

EXAMPLE 1

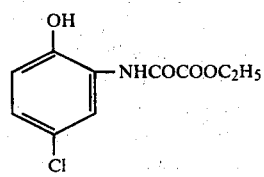

A solution of 2.7 g of ethyl oxalylchloride in 6 ml of benzene was added dropwise to a solution of 3 g of 2-amino-4-chlorophenol and 3 ml of pyridine in 30 ml of tetrahydrofuran with stirring under cooling to 0°–10° C. After the addition was finished, the reaction mixture was stirred for one hour at room temperature and then 50 ml of toluene and 100 ml of water were successively added to the reaction mixture. Crystals thus formed were recovered by filtration from the reaction mixture, washed with water, and recrystallized from ethanol to provide 2.8 g of the white crystals of ethyl 5-chloro-2-hydroxyoxanilate.

Elemental analysis for $C_{10}H_{10}NO_4Cl$:

|  | C (%) | H (%) | N (%) |
| --- | --- | --- | --- |
| Calculated: | 49.30 | 4.14 | 5.75 |
| Found: | 49.02 | 4.01 | 5.69 |

Nuclear magnetic resonance spectra (DMSO-$d_6$) δ: 1.31 (3H, t, —CH$_3$), 4.29 (2H, q, —CH$_2$—), 6.91 (1H, d, H at the 6-position of benzene ring), 7.05 (1H, dd, H at the 4-position of benzene ring), 8.01 (1H, d, H at the 3-position of benzene ring).

EXAMPLE 2

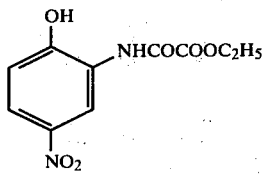

By following the same procedure as in Example 1 using 3 g of 2-amino-4-nitrophenol and 2.7 g of ethyl oxalyl chloride as the starting materials, 4.0 g of the white crystals of 2-hydroxy-5-nitrooxanilate were obtained.

Melting point: 280° C. (decomposed).

Nuclear magnetic resonance spectra (DMSO-$d_6$) δ: 1.32 (3H, t, —CH$_3$), 4.31 (2H, q, —CH$_2$—), 7.05 (1H, d, H at the 6-position of benzene ring), 7.95 (1H, dd, H at the 4-position of benzene ring), 8.87 (1H, d, H at the 3-position of benzene ring).

EXAMPLE 3

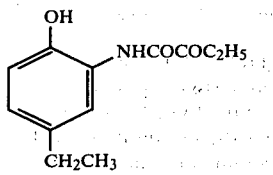

To a mixture of 60 ml of methylene chloride and 3 ml of pyridine was added 3 g of 2-amino-4-ethylphenol hydrochloride and then a solution of 2.3 g of ethyloxalyl chloride in 30 ml of methylene chloride was added thereto at temperatures below 10° C. After stirring the reaction mixture for 3 hours, the reaction mixture was washed with water, 5% hydrochloric acid, and then water, dried over anhydrous magnesium sulfate, and concentrated under reduced pressure. Crystals thus formed were recovered and recrystallized from ethanol to provide 1.9 g of ethyl 5-ethyl-2-hydroxyoxanilate.

Elemental analysis for $C_{12}H_{15}NO_4$:

|  | C (%) | H (%) | N (%) |
| --- | --- | --- | --- |
| Calculated: | 60.75 | 6.37 | 5.90 |
| Found: | 60.59 | 6.46 | 5.95 |

Nuclear magnetic resonance spectra (CDCl$_3$) δ: 1.20 (3H, t, —CH$_2$CH$_3$), 1.41 (3H, t, COOCH$_2$CH$_3$), 2.58 (2H, q, —CH$_2$CH$_3$), 4.42 (2H, q, —COOCH$_2$CH$_3$), 6.90 (2H, m, H at the 3- and 4-positions of benzene ring), 7.28 (1H, d, H at the 6-position of benzene ring).

EXAMPLE 4

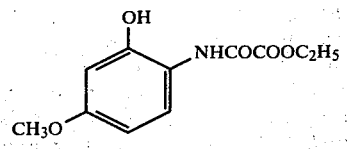

By following the same procedure as in Example 1 using 2 g of 2-amino-5-methoxyphenol and 2.7 g of ethyl oxalyl chloride, 2.13 g of ethyl 2-hydroxy-4-methoxyoxanilate was obtained.

Elemental analysis for $C_{11}H_{13}NO_5$:

|  | C (%) | H (%) | N (%) |
| --- | --- | --- | --- |
| Calculated: | 55.23 | 5.48 | 5.85 |
| Found: | 55.08 | 5.47 | 5.83 |

Mass spectrum: m/e: 239(M+).

EXAMPLE 5

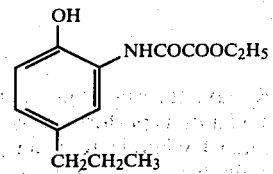

A solution of 2.5 g of ethyl oxalyl chloride in 15 ml of methylene chloride was added dropwise to a solution of 3.4 g of 2-amino-4-(n-propyl)phenol hydrochloride and 3 ml of pyridine in a mixture of 80 ml of methylene chloride and 30 ml of tetrahydrofuran with stirring under cooling to 0°–10° C. After the addition was finished, the reaction mixture was stirred for 3 hours at room temperature, washed with water, 5% hydrochloric acid, and then water, dried over anhydrous magnesium sulfate, and concentrated under reduced pressure. Crystals formed were recovered and recrystallized from ethanol to provide 3.4 g of ethyl 2-hydroxy-5-n-propyloxanilate.

Melting point: 155°–160° C.

Elemental analysis for $C_{13}H_{17}NO_4$:

|  | C (%) | H (%) | N (%) |
| --- | --- | --- | --- |
| Calculated: | 62.14 | 6.82 | 5.57 |
| Found: | 61.89 | 7.02 | 5.53 |

Mass spectrum: m/e: 251(M+).

By following the same procedure as Example 5, compounds of following Examples 6–15 were prepared.

EXAMPLE 6

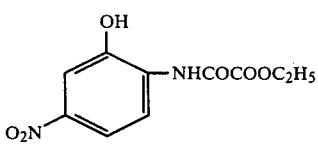

Ethyl 2-hydroxy-4-nitrooxanilate

Melting point: 269°–271° C. (decomposed).
Elemental analysis for $C_{10}H_{10}N_2O_6$:

|  | C (%) | H (%) | N (%) |
|---|---|---|---|
| Calculated: | 47.25 | 3.97 | 11.02 |
| Found: | 47.11 | 3.96 | 11.07 |

EXAMPLE 7

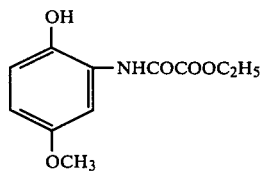

Ethyl 2-hydroxy-5-methoxyoxanilate

Mass spectrum m/e: 239(M+).
Elemental analysis for $C_{11}H_{13}NO_5$:

|  | C (%) | H (%) | N (%) |
|---|---|---|---|
| Calculated: | 55.23 | 5.48 | 5.85 |
| Found: | 55.10 | 5.45 | 5.96 |

EXAMPLE 8

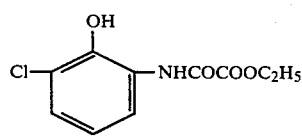

Ethyl 3-chloro-2-hydroxyoxanilate

Melting point: 161°–163° C.
Elemental analysis for $C_{10}H_{10}NO_4Cl$:

|  | C (%) | H (%) | N (%) | Cl (%) |
|---|---|---|---|---|
| Calculated: | 49.30 | 4.14 | 5.75 | 14.55 |
| Found: | 49.22 | 4.09 | 5.81 | 14.33 |

EXAMPLE 9

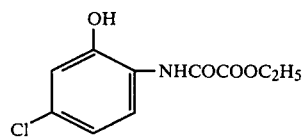

Ethyl 4-chloro-2-hydroxyoxanilate

Melting point: above 300° C.
Elemental analysis for $C_{10}H_{10}NO_4Cl$:

|  | C (%) | H (%) | N (%) |
|---|---|---|---|
| Calculated: | 49.30 | 4.14 | 5.75 |
| Found: | 49.19 | 4.00 | 5.88 |

EXAMPLE 10

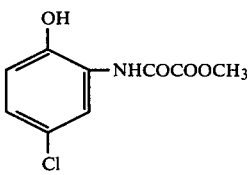

Methyl 5-chloro-2-hydroxyoxanilate

Melting point: above 300° C.
Elemental analysis for $C_9H_8NO_4Cl$:

|  | C (%) | H (%) | N (%) | Cl (%) |
|---|---|---|---|---|
| Calculated: | 47.08 | 3.51 | 6.10 | 15.44 |
| Found: | 46.91 | 3.21 | 6.08 | 15.30 |

EXAMPLE 11

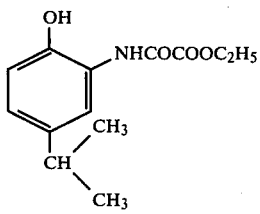

Ethyl 2-hydroxy-5-isopropyloxanilate

Melting point: 150°–155° C.
Elemental analysis for $C_{13}H_{17}NO_4$:

|  | C (%) | H (%) | N (%) |
|---|---|---|---|
| Calculated: | 62.14 | 6.82 | 5.57 |
| Found: | 62.03 | 6.74 | 5.77 |

EXAMPLE 12

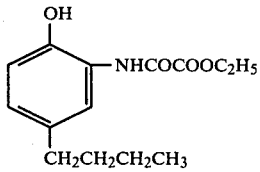

Ethyl 5-n-butyl-2-hydroxyoxanilate

Melting point: 135°–140° C.
Elemental analysis for $C_{14}H_{19}NO_4$:

|  | C (%) | H (%) | N (%) |
|---|---|---|---|
| Calculated: | 63.38 | 7.22 | 5.28 |

EXAMPLE 13

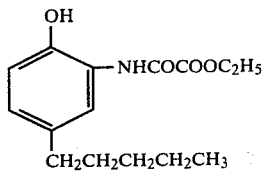

Ethyl 5-n-amyl-2-hydroxyoxanilate

Melting point: 135°–138° C.
Elemental analysis for $C_{15}H_{21}NO_4$:

|  | C (%) | H (%) | N (%) |
|---|---|---|---|
| Calculated: | 64.50 | 7.58 | 5.01 |
| Found: | 64.29 | 7.78 | 4.96 |

EXAMPLE 14

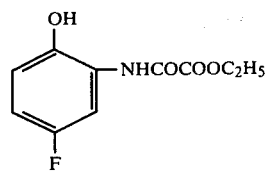

Ethyl 5-fluoro-2-hydroxyoxanilate

Melting point: 262°–265° C.
Elemental analysis for $C_{10}H_{10}NO_4F$:

|  | C (%) | H (%) | N (%) |
|---|---|---|---|
| Calculated: | 52.87 | 4.44 | 6.17 |
| Found: | 52.64 | 4.24 | 6.35 |

EXAMPLE 15

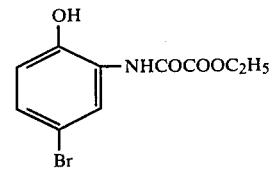

Ethyl 5-bromo-2-hydroxyoxanilate

Melting point: above 300° C.
Elemental analysis for $C_{10}H_{10}NO_4Br$:

|  | C (%) | H (%) | N (%) |
|---|---|---|---|
| Calculated: | 41.69 | 3.50 | 4.86 |
| Found: | 41.70 | 3.26 | 4.96 |

-continued

|  | C (%) | H (%) | N (%) |
|---|---|---|---|
| Found: | 63.26 | 7.14 | 5.40 |

EXAMPLE 16

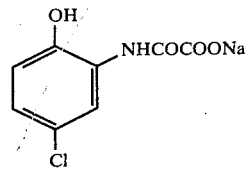

A mixture of 2 g of ethyl 5-chloro-2-hydroxyoxanilate, 50 ml of ethanol, and 8.2 ml of a 1 normal sodium hydroxide solution was stirred for one hour at 60° C. The reaction mixture was concentrated under reduced pressure and the crystals formed were recovered and dissolved in 100 ml of water. Activated carbon was added to the solution and after filtering the mixture, the filtrate was concentrated under reduced pressure to 10 ml. After adding 10 ml of water to the concentrate, the mixture was allowed to stand overnight and the crystals formed were recovered by filtration to provide 1.1 g of sodium 5-chloro-2-hydroxyoxanilate.

Melting point: >300° C.
Elemental analysis for $C_8H_5NO_4ClNa$:

|  | C (%) | H (%) | N (%) | Cl (%) |
|---|---|---|---|---|
| Calculated: | 40.45 | 2.12 | 5.90 | 14.92 |
| Found: | 40.37 | 2.03 | 5.83 | 14.79 |

EXAMPLE 17

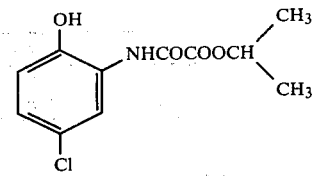

A mixture of 2 g of ethyl 5-chloro-2-hydroxyoxanilate, 100 ml of isopropyl alcohol, and 100 mg of p-toluenesulfonic acid was refluxed for 24 hours. The reaction mixture was allowed to cool to room temperature and then allowed to stand overnight. Crystals formed were recovered by filtration and recrystallized from isopropyl alcohol to provide 1.1 g of isopropyl 5-chloro-2-hydroxyoxanilate.

Melting point: >300° C.
Elemental analysis for $C_{11}H_{12}NO_4Cl$:

|  | C (%) | H (%) | N (%) | Cl (%) |
|---|---|---|---|---|
| Calculated: | 51.27 | 4.69 | 5.44 | 13.76 |
| Found: | 51.20 | 4.58 | 5.34 | 13.88 |

EXAMPLE 18

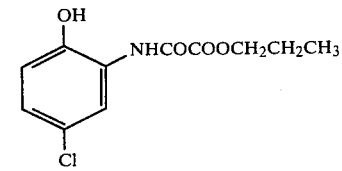

A mixture of 2.5 g of ethyl 5-chloro-2-hydroxyoxanilate, 200 mg of p-toluenesulfonic acid, and 100 ml of n-propanol was stirred for 2 days at 100° C. The reaction mixture was concentrated under reduced pressure and the residue was washed with ether and recrystallized from n-propanol to provide 0.9 g of n-propyl 5-chloro-2-hydroxyoxanilate.

Mass spectrum: m/e: 257(M+).
Elemental analysis for $C_{11}H_{12}NO_4Cl$:

|  | C (%) | H (%) | N (%) |
|---|---|---|---|
| Calculated: | 51.27 | 4.69 | 5.44 |
| Found: | 51.18 | 4.43 | 5.84 |

By following the same procedure as Example 18, compounds of following Examples 19 and 20 were prepared.

EXAMPLE 19

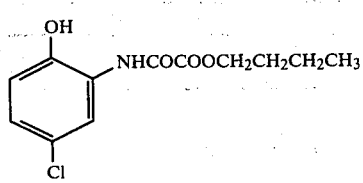

n-Butyl 5-chloro-2-hydroxyoxanilate

Mass spectrum m/e: 271(M+).
Elemental analysis for $C_{12}H_{14}NO_4Cl$:

|  | C (%) | H (%) | N (%) |
|---|---|---|---|
| Calculated: | 53.05 | 5.19 | 5.16 |
| Found: | 52.80 | 5.11 | 5.27 |

EXAMPLE 20

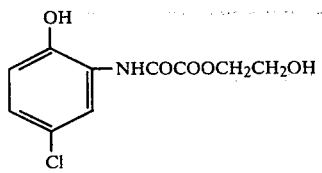

2-Hydroxyethyl 5-chloro-2-hydroxyoxanilate

Melting point: above 300° C.
Elemental analysis for $C_{10}H_{10}NO_5Cl$:

|  | Cl (%) |
|---|---|
| Calculated: | 13.65 |
| Found: | 13.83 |

EXAMPLE 21

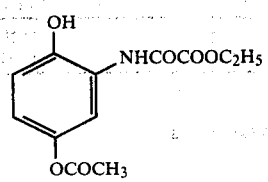

A solution of 1.25 g of ethyl oxalyl chloride in 10 ml of methylene chloride was added dropwise to a solution of 1.4 g of 4-acetoxy-2-aminophenol and 1.1 ml of pyridine in 30 ml of tetrahydrofuran at a temperature below 10° C. After the addition was finished, the reaction temperature was allowed to raise to room temperature and stirred for 3 hours. The reaction mixture was concentrated under reduced pressure and the residue was washed with diluted hydrochloric acid, washed with water, and recrystallized from a mixture of tetrahydrofuran and n-hexane to provide 1.7 g of ethyl 5-acetoxy-2-hydroxyoxanilate.

Mass spectrum: m/e: 267(M+).
Elemental analysis for $C_{12}H_{13}NO_6$:

|  | C (%) | H (%) | N (%) |
|---|---|---|---|
| Calculated: | 53.93 | 4.90 | 5.24 |
| Found: | 53.78 | 4.72 | 5.22 |

By following the same procedure as Example 21, compounds of following Examples 22-25 were prepared.

EXAMPLE 22

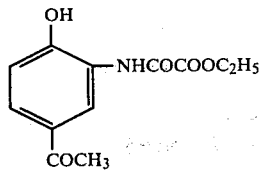

Ethyl 5-acetyl-2-hydroxyoxanilate

Melting point: 263°-265° C. (decomposed).
Elemental analysis for $C_{12}H_{13}NO_5$:

|  | C (%) | H (%) | N (%) |
|---|---|---|---|
| Calculated: | 57.37 | 5.22 | 5.58 |
| Found: | 57.35 | 5.14 | 5.74 |

EXAMPLE 23

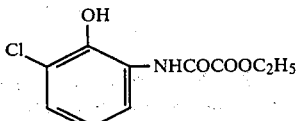

Ethyl 3,5-dichloro-4-hydroxyoxanilate

Mass spectrum m/e: 277(M+).
Elemental analysis for $C_{10}H_9NO_4Cl$:

| | C (%) | H (%) | N (%) | Cl (%) |
|---|---|---|---|---|
| Calculated: | 43.19 | 3.26 | 5.04 | 25.50 |
| Found: | 42.99 | 3.13 | 5.03 | 25.65 |

EXAMPLE 24

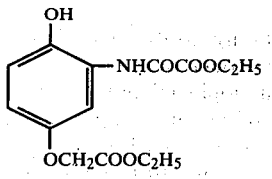

Ethyl 5-ethoxycarbonylmethoxy-2-hydroxyoxanilate

Melting point: 191°–193° C.
Elemental analysis for $C_{14}H_{17}NO_7$:

| | C (%) | H (%) | N (%) |
|---|---|---|---|
| Calculated: | 54.02 | 5.50 | 4.50 |
| Found: | 53.66 | 5.60 | 4.50 |

EXAMPLE 25

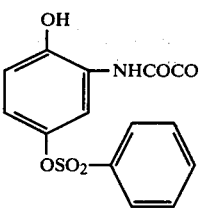

Ethyl 2-hydroxy-5-phenylsulfonyloxyoxanilate

Melting point: 196°–199° C.
Elemental analysis for $C_{16}H_{15}NO_7S$:

| | C (%) | H (%) | N (%) | S (%) |
|---|---|---|---|---|
| Calculated: | 52.60 | 4.14 | 3.83 | 8.77 |
| Found: | 52.35 | 3.98 | 3.63 | 8.96 |

EXAMPLE 26

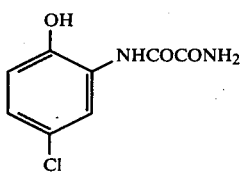

A mixture of 2 g of ethyl 5-chloro-2-hydroxyoxanilate, 150 ml of methanol and 20 ml of concentrated aqueous ammonia was stirred for one hour at room temperature. The reaction mixture formed was concentrated under reduced pressure and crystals were recrystallized from 50% ethanol to provide 1.2 g of 5-chloro-2-hydroxyoxanylamide.
Melting point: 247° C.
Elemental analysis for $C_8H_7N_2O_3Cl$:

| | C (%) | H (%) | N (%) | Cl (%) |
|---|---|---|---|---|
| Calculated: | 44.77 | 3.29 | 13.05 | 16.52 |
| Found: | 44.74 | 3.05 | 13.09 | 16.72 |

By following the same procedure as Example 26, compounds of following Examples 27-30 were prepared.

EXAMPLE 27

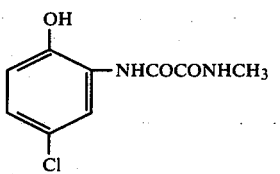

5-Chloro-2-hydroxy-N—methyloxanilamide

Melting point: 280°–283° C.
Elemental analysis for $C_9H_9N_2O_3Cl$:

| | C (%) | H (%) | N (%) | Cl (%) |
|---|---|---|---|---|
| Calculated: | 47.28 | 3.97 | 12.25 | 15.51 |
| Found: | 47.21 | 3.73 | 12.16 | 15.61 |

EXAMPLE 28

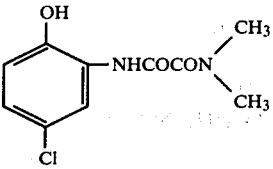

5-Chloro-2-hydroxy-N,N—dimethyloxanylamide

Melting point: 193°–196° C.
Elemental analysis for $C_{10}H_{11}N_2O_3Cl$:

| | C (%) | H (%) | N (%) | Cl (%) |
|---|---|---|---|---|
| Calculate: | 49.50 | 4.57 | 11.54 | 14.61 |
| Found: | 49.22 | 4.51 | 11.43 | 14.86 |

EXAMPLE 29

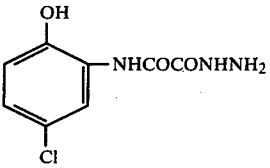

5-Chloro-2-hydroxyoxanilohydrazide

Melting point: above 300° C.
Elemental analysis for $C_8H_8N_3O_3Cl$:

| | N (%) |
|---|---|
| Calculate: | 18.30 |

| | N (%) |
|---|---|
| Found: | 18.20 |

EXAMPLE 30

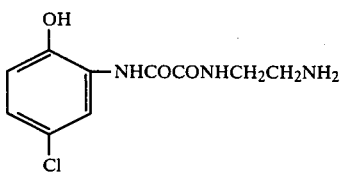

5-Chloro-2-hydroxy-N—(2-aminoethyl)oxanilamide

Mass spectrum m/e: 257(M+):
Elemental analysis for $C_{10}H_{12}N_3O_3Cl$:

| | C (%) | H (%) | N (%) | Cl (%) |
|---|---|---|---|---|
| Calculated: | 46.61 | 4.69 | 16.31 | 13.76 |
| Found: | 46.43 | 4.77 | 16.13 | 13.82 |

EXAMPLE 31

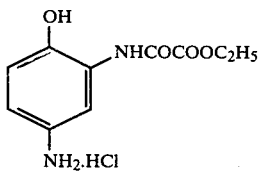

A solution of 3 g of ethyl 2-hydroxy-5-nitrooxanilate in 50 ml of ethanol was catalytically hydrogenated in the presence of 0.5 g of 10% palladium carbon. After the absorption of hydrogen stopped, the catalyst was filtered off and 6 ml of a mixture of 2N-HCl ethanol was added to the filtrate. After concentrating the mixture under reduced pressure, the solid formed was washed with a small amount of ethanol and dried to provide 2.2 g of ethyl 5-amino-2-hydroxyoxanilate hydrochloride.
Melting point: 250°-260° C. (decompd.).
Elemental analysis for $C_{10}H_{13}N_2O_4Cl$:

| | C (%) | H (%) | N (%) | Cl (%) |
|---|---|---|---|---|
| Calculated: | 46.08 | 5.03 | 10.75 | 13.60 |
| Found: | 45.95 | 4.91 | 10.58 | 13.58 |

EXAMPLE 32

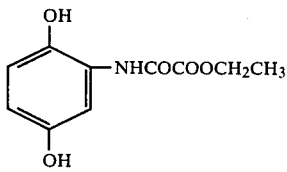

After catalytically reducing 2.5 g of 2-nitroquinol in 50 ml of tetrahydrofuran in the presence of 10% palladium-carbon until the absorption of hydrogen stopped, the catalyst was filtered off and 3 ml of pyridine was added to the filtrate. To the solution was added dropwise a solution of 2.5 g of ethyl oxalyl chloride in 10 ml of methylene chloride at a temperature below 15° C. Thereafter, the reaction mixture was stirred for 3 hours at room temperature. After removing the insoluble material by filtration, the filtrate was concentrated under reduced pressure and the residue was mixed with 50 ml of diluted hydrochloric acid followed by stirring for one hour at room temperature. Crystals formed were recovered by filtration, washed with water and then ethanol, and recrystallized from ethanol to provide 0.7 g of ethyl 2,5-dihydroxyoxanilate.
Melting point: >300° C.
Elemental analysis for $C_{10}H_{11}NO_5$:

| | N (%) |
|---|---|
| Calculated: | 6.22 |
| Found: | 5.96 |

EXAMPLE 33

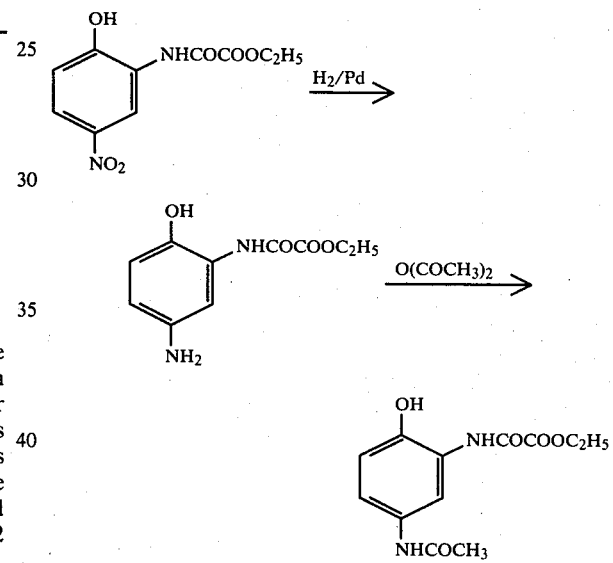

A solution of 2.8 g of ethyl 2-hydroxy-5-nitrooxanilate in 40 ml of tetrahydrofuran was catalytically hydrogenated in the presence of 0.3 g of 10% palladium carbon until the absorption of hydrogen stopped. After the reaction was over, the catalyst was filtered off and to the filtrate was added 3.5 ml of acetic anhydride under cooling below −20° C. The mixture was further stirred for 30 minutes at room temperature and crystals formed were recovered by filtration, washed with tetrahydrofuran, and dried to provide 2.2 g of ethyl 5-acetamido-2-hydroxyoxanilate.
Melting point: >300° C. (decompd.).
Elemental analysis for $C_{12}H_{14}N_2O_5$:

| | C (%) | H (%) | N (%) |
|---|---|---|---|
| Calculated: | 54.13 | 5.30 | 10.52 |
| Found: | 54.09 | 5.25 | 10.70 |

By following the same procedure as in Example 33, the compounds in following Examples 34–36 were produced.

EXAMPLE 34

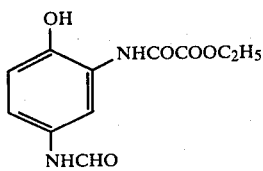

By following the above-described procedure using a mixture of acetic anhydride and formic acid (5:3 V/V) in place of acetic anhydride in Example 33, 2.1 g of ethyl 5-formamido-2-hydroxyoxanilate was obtained.

Melting point: >300° C. (decompd.).
Elemental analysis for $C_{11}H_{12}N_2O_5$:

|  | C (%) | H (%) | N (%) |
|---|---|---|---|
| Calculated: | 52.38 | 4.80 | 11.11 |
| Found: | 52.26 | 4.59 | 11.26 |

EXAMPLE 35

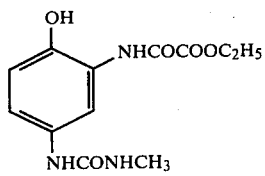

By following the above-described procedure using methyl isocyanate in place of acetic anhydride in Example 33, ethyl 2-hydroxy-5-(3-methylureido)oxanilate was obtained.

Melting point: 235°–236° C. (decompd.)
Elemental analysis for $C_{12}H_{15}N_3O_5$:

|  | C (%) | H (%) | N (%) |
|---|---|---|---|
| Calculated: | 51.24 | 5.38 | 14.94 |
| Found: | 51.04 | 5.32 | 15.01 |

EXAMPLE 36

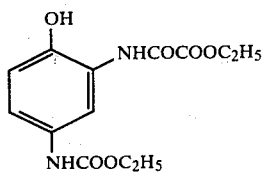

By following the above-described procedure using ethyl chlorocarbonate and pyridine in place of acetic anhydride in Example 33, 5-ethoxycarbonylacido-2-hydroxyoxanilate was obtained.

Melting point: 257°–259° C. (decompd.).
Elemental analysis for $C_{12}H_{14}N_2O_6$:

|  | C (%) | H (%) | N (%) |
|---|---|---|---|
| Calculated: | 51.06 | 5.00 | 9.92 |
| Found: | 51.18 | 5.09 | 9.69 |

EXAMPLE 37

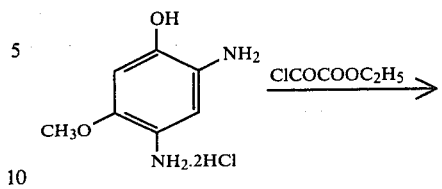

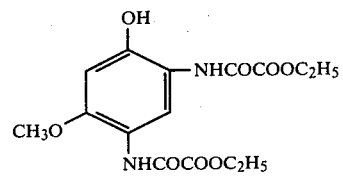

To a mixture of 1 g of 4,6-diaminoresorcinol monomethyl ether dihydrochloride, 2 ml of pyridine, and 10 ml of methylene chloride was added dropwise a mixture of 1.5 g of ethyloxalyl chloride and 10 ml of methylene chloride at a temperature below 5° C. After the addition was finished, the reaction mixture was stirred for 3 hours at room temperature. The reaction mixture was washed with water, dried over anhydrous magnesium sulfate, and concentrated under reduced pressure. The residue was recrystallized from ethanol to provide 0.9 g of ethyl 5-ethoxyoxalylamido-2-hydroxy-4-methoxyoxanilate.

Melting point: 274°–277° C.
Elemental analysis for $C_{15}H_{18}N_2O_8$:

|  | C (%) | H (%) | N (%) |
|---|---|---|---|
| Calculated: | 50.85 | 5.12 | 7.91 |
| Found: | 50.64 | 5.15 | 7.81 |

EXAMPLE 38

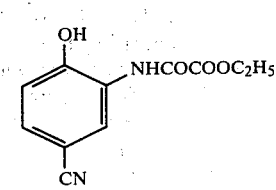

In 25 ml of tetrahydrofuran was dissolved 2.5 g of 4-cyano-2-nitrophenol and then the catalytic reduction was performed using 0.25 g of 10% palladium carbon as a catalyst until the absorption of hydrogen stopped. After the reaction was over, the catalyst was filtered off and to the filtrate containing 2-amino-4-cyanophenol was added dropwise a mixture of 2.5 g of ethyl oxalyl chloride and 4 ml of toluene with stirring under cooling below −10° C. After the addition was finished, the reaction mixture was stirred for 2 hours at room temperature and crystals formed were recovered by filtration, washed with water and then propanol, and recrystallized from methyl cellosolve to provide 2.1 g of ethyl 5-cyano-2-hydroxyoxanilate.

Melting point: 295° C. (decompd.).
Elemental analysis for $C_{11}H_{10}N_2O_4$:

|  | C (%) | H (%) | N (%) |
|---|---|---|---|
| Calculated: | 56.41 | 4.30 | 11.96 |

| | C (%) | H (%) | N (%) |
|---|---|---|---|
| Found: | 56.42 | 4.21 | 11.96 |

By following the same procedure as Example 38, compounds of following Examples 39 and 40 were prepared.

EXAMPLE 39

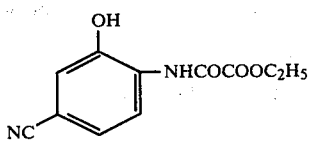

Ethyl 4-cyano-2-hydroxyoxanilate

Melting point: above 300° C.
Elemental analysis for $C_{11}H_{10}N_2O_4$:

| | C (%) | H (%) | N (%) |
|---|---|---|---|
| Calculated: | 56.41 | 4.30 | 11.96 |
| Found: | 56.34 | 4.35 | 11.86 |

EXAMPLE 40

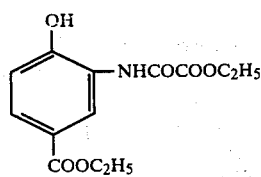

Ethyl 5-ethoxycarbonyl-2-hydroxyoxanilate

Melting point: 245°-246° C. (ethanol-toluene).
Elemental analysis for $C_{13}H_{15}NO_6$:

| | C (%) | H (%) | N (%) |
|---|---|---|---|
| Calculated: | 55.51 | 5.38 | 4.98 |
| Found: | 55.40 | 5.32 | 5.08 |

EXAMPLE 41

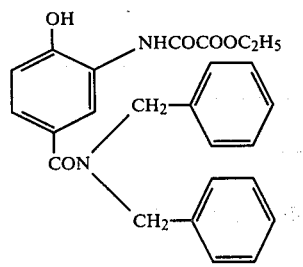

By reducing N,N-dibenzyl-4-benzyloxy-3-nitrobenzamide (melting point 131°-132° C.) in water-containing methanol with reduced iron powder-hydrochloric acid, 3-amino-N,N-dibenzyl-4-benzyloxybenzamide (melting point 81° C.) was obtained. Then, by reacting 3-amino-N,N-dibenzyl-4-benzyloxybenzamide with ethyl oxalyl chloride in the presence of pyridine in tetrahydrofuran, ethyl 2-benzyloxy-5-(N,N-dibenzylcarbamoyl)oxanilate (melting point 132°-133° C.) was obtained. A solution of 3.6 g of ethyl 2-benzyloxy-5-(N,N-dibenzylcarbamoyl)oxanilate thus obtained in 100 ml of ethanol was catalytically hydrogenated in the presence of 0.8 g of 10% palladium carbon until the absorption of hydrogen stopped. After the reaction was over, the catalyst was filtered off and the filtrate was concentrated under reduced pressure to provide 2.7 g of ethyl 5-(N,N-dibenzylcarbamoyl)-2-hydroxyoxanilate, a gum.

Nuclear magnetic resonance spectra (CDCl$_3$) δ: 1.40 (3H, t, —CH$_3$), 4.36 (2H, q, —C$\underline{H}_2$CH$_3$), 4.57

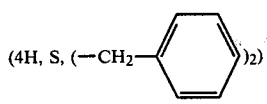

(4H, S, (—CH$_2$— ⌬ )$_2$)

6.64 (1H, d, H at the 3-position of benzene ring), 7.04 (1H, d, d, H at the 4-position of benzene ring), 7.1-7.5

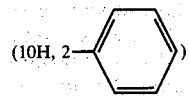

(10H, 2— ⌬ )

8.38 (1H, d, H at the 6-position of benzene ring), 9.42 and 9.90 (each 1H, —OH and —NH—).

In addition, N,N-dibenzyl-4-benzyloxy-3-nitrobenzamide which was used as the starting material in this example was obtained by the reaction of 4-benzyloxy-3-nitrobenzoyl chloride with N,N'-dibenzylamine.

EXAMPLE 42

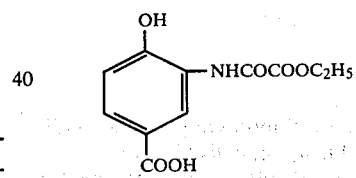

By reducing 4-benzyloxy-3-nitrobezncoic acid benzyl ester (melting point 68°-70° C.) with reduced iron powder-hydrochloric acid in 90% methanol, 3-amino-4-benzyloxybenzoic acid benzyl ester (melting point 79°-81° C.) was obtained and further by reacting the product with ethyl oxalyl chloride in the presence of pyridine in tetrahydrofuran, 2-benzyloxy-5-benzyloxycarbonyl oxanilate (melting point 136°-138° C.) was obtained.

Then, 1.8 g of ethyl 2-benzyloxy-5-benzyloxycarbonyl oxanilate thus obtained was dissolved in 50 ml of ethanol and catalytically hydrogenated in the presence of 0.3 g of 10% palladium carbon until the absorption of hydrogen stopped. After the reaction was over, the catalyst was filtered off and the filtrate was concentrated under reduced pressure. Crystals formed were washed with isopropanol and dried to provide 0.9 g of ethyl 5-carboxy-2-hydroxyoxanilate.

Melting point: >300° C.
Elemental analysis for $C_{11}H_{11}NO_6$:

| | C (%) | H (%) | N (%) |
|---|---|---|---|
| Calculated: | 52.18 | 4.38 | 5.53 |

| | C (%) | H (%) | N (%) |
|---|---|---|---|
| Found: | 51.93 | 4.45 | 5.76 |

In addition, the 4-benzyloxy-3-nitrobenzoic acid benzyl ester which was used as the starting material in this example was obtained through the steps of benzylation, hydrolysis and benzylation of 4-hydroxy-3-nitrobenzoic acid ethyl ester.

EXAMPLE 43

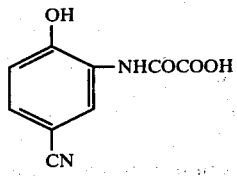

To a mixture of 30 ml of 4% potassium hydroxide solution and 30 ml of methanol was added 2 g of ethyl 5-cyano-2-hydroxyoxanilate and the mixture was stirred overnight at room temperature. To the reaction mixture was added 15 ml of 10% hydrochloric acid solution and white crystals formed were recovered by filtration and recrystallized from water to provide 1.2 g of 5-cyano-2-hydroxyoxanilic acid.

Melting point: >300° C.
Mass spectrum (FD): m/e: 206(M+).

EXAMPLE 44

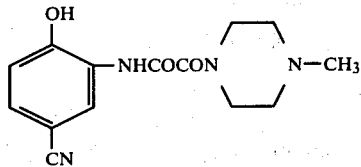

To a mixture of 1.2 g of N-methylpiperazine and 20 ml of methanol was added gradually 2 g of ethyl 5-cyano-2-hydroxyoxanilate and after stirring the mixture for 3 hours at room temperature, crystals formed were recovered by filtration, washed successively with isoporpnaol and ether, and dried to provide 2 g of 1-(5-cyano-2-hydroxyoxanilyl)-4-methylpiperazine.

Melting point: 256° C.
Elemental analysis for $C_{14}H_{16}N_4O_3$:

| | C (%) | H (%) | N (%) |
|---|---|---|---|
| Calculated: | 58.32 | 5.59 | 19.43 |
| Found: | 58.11 | 5.51 | 19.39 |

EXAMPLE 45

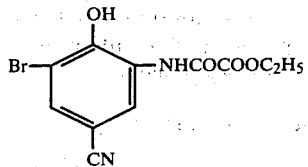

A mixture of 1.1 g of bromine and 5 ml of acetic acid was added dropwise to a solution of 1.5 g of ethyl 5-cyano-2-hydroxyoxanilate and 1 g of sodium acetate in a mixed solution of 10 ml of dimethyl sulfoxide, 10 ml of methanol and 20 ml of acetic acid. After stirring the mixture for 30 minutes at room temperature, 6 ml of 2 normal hydrochloric acid and 200 ml of water were added to the reaction mixture and the product was extracted with a mixture of 30 ml of toluene and 40 ml of ethyl acetate. The extract was washed with water, dried, and then concentrated under reduced pressure. Crystals formed were washed with a mixture of ether and n-hexane to provide 1.5 g of ethyl 3-bromo-5-cyano-2-hydroxyoxanilate.

Starting point: 163°-165° C.
Elemental analysis for $C_{11}H_9N_2O_4Br$:

| | C (%) | H (%) | N (%) | Br (%) |
|---|---|---|---|---|
| Calculated: | 42.20 | 2.90 | 8.95 | 25.52 |
| Found: | 42.58 | 2.73 | 9.02 | 25.68 |

EXAMPLE 46

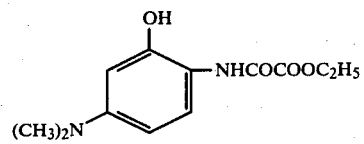

In 40 ml of methanol was dissolved 2 g of 2-nitroso-5-dimethylaminophenol hydrochloride and catalytically hydrogenated in the presence of 0.15 g of 10% palladium carbon as a catalyst until the absorption of hydrogen stopped. After the reaction was over, the catalyst was filtered off and the filtrate was concentrated under reduced pressure. After dissolving 1.9 g of the amorphous powder of 2-amino-5-dimethylaminophenol hydrochloride thus obtained in 30 ml of pyridine, a mixture of 1.5 g of ethyl oxalyl chloride and 5 ml of toluene was added dropwise to the solution under cooling to temperatures below 0° C. After the addition was finished, the reaction mixture was stirred overnight at room temperature and crystals thus formed were recovered by filtration, washed successively with water and isopropanol, and dried to provide 1.3 g of ethyl 4-dimethylamino-2-hydroxyoxanilate.

Melting point: 259°-260° C. (decompd.).
Elemental analysis for $C_{12}H_{16}N_2O_4$:

| | C (%) | H (%) | N (%) |
|---|---|---|---|
| Calculated: | 57.13 | 6.39 | 11.10 |
| Found: | 56.88 | 6.29 | 11.20 |

EXAMPLE 47

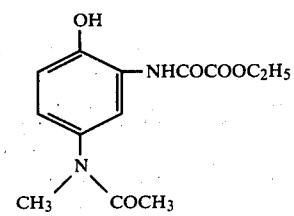

In 30 ml of tetrahydrofuran was dissolved 2.1 g of 4-benzyloxy-N-methyl-3-nitroacetanilide obtained by benzylating and then methylating 4-hydroxy-3-nitroacetanilide and was catalytically hydrogenated in the presence of 0.2 g of 10% palladium carbon as a catalyst until the absorption of hydrogen stopped. After the reaction was over, the reaction mixture was filtered to remove the catalyst and 2 ml of pyridine was added to the filtrate. Then, to the mixture was gradually added a mixture of 1.2 g of ethyl oxalyl chloride and 5 ml of toluene under cooling below $-10°$ C. and the resultant mixture was stirred for 2 hours at room temperature. The reaction mixture was concentrated under reduced pressure and the residue obtained was extracted with 50 ml of a mixture of toluene and ethyl acetate (1:1). After washing the extract with water followed by drying, the solvent was distilled off. To the residue formed was added isopropanol and crystals thus formed were recovered by filtration, washed with isopropanol, and dried to provide 0.6 g of ethyl 5-(N-acetylmethylamino)-2-hydroxyoxanilate.

Melting point: 190°–192° C.

Elemental analysis for $C_{13}H_{16}N_2O_5$:

|  | C (%) | H (%) | N (%) |
|---|---|---|---|
| Calculated: | 55.71 | 5.75 | 9.99 |
| Found: | 55.83 | 5.83 | 9.84 |

What is claimed is:

1. A 2-hydroxyoxanilic acid derivative represented by the following formula and the pharmaceutically acceptable salts thereof:

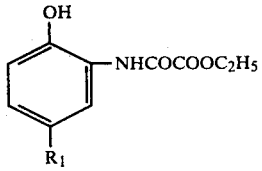

wherein $R_1$ is an amino group, an acetamido group, or a cyano group.

2. Ethyl 5-amino-2-hydroxyoxanilate.
3. Ethyl 5-acetamido-2-hydroxyoxanilate.
4. Ethyl 5-cyano-2-hydroxyoxanilate.

* * * * *